(12) United States Patent
Widmann et al.

(10) Patent No.: US 8,991,156 B2
(45) Date of Patent: Mar. 31, 2015

(54) METHOD AND STORAGE CONTAINER FOR DETERMINING A STORED AMOUNT OF AMMONIA FOR CATALYTIC EXHAUST GAS PURIFICATION

(75) Inventors: Ralf Widmann, Haimhausen (DE); Thomas Baumeister, Munich (DE); Andreas Bruhn, Puchheim (DE); Udo Strathoff, Munich (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 723 days.

(21) Appl. No.: 13/293,362

(22) Filed: Nov. 10, 2011

(65) Prior Publication Data

US 2012/0049852 A1  Mar. 1, 2012

Related U.S. Application Data

(63) Continuation of application No. PCT/EP2010/055450, filed on Apr. 23, 2010.

(30) Foreign Application Priority Data

May 27, 2009 (DE) .......................... 10 2009 022 884

(51) Int. Cl.
*F01N 3/00* (2006.01)
*F01N 3/10* (2006.01)
(Continued)

(52) U.S. Cl.
CPC .............. *F01N 11/00* (2013.01); *F01N 3/2066* (2013.01); *B01D 2251/2062* (2013.01); *F01N 2610/02* (2013.01); *F01N 2900/1814* (2013.01); *Y02T 10/47* (2013.01); *Y02T 10/24* (2013.01)
USPC ............... 60/295; 60/301; 324/444; 324/448; 324/449

(58) Field of Classification Search
USPC ........... 60/295, 301; 324/71.1, 439, 444, 448, 324/449
See application file for complete search history.

(56) References Cited

U.S. PATENT DOCUMENTS 6,004,524 A    12/1999  Morsbach et al.
6,387,336 B2    5/2002  Marko et al.
(Continued)

FOREIGN PATENT DOCUMENTS

DE       42 03 219 A1    8/1993
DE      197 28 343 C1    4/1999
(Continued)

OTHER PUBLICATIONS

International Search Report dated Jul. 22, 2010 with English translation (four (4) pages).

(Continued)

*Primary Examiner* — Audrey K Bradley
(74) *Attorney, Agent, or Firm* — Crowell & Moring LLP

(57) ABSTRACT

A method is provided for determining the amount of ammonia which is stored in a storage container by a chemical bond to a solid storage medium, in particular a salt of an earth alkaline metal or the like, and which can be released by supplying heat in order to be supplied to a catalytic exhaust gas purification device of an internal-combustion engine. The storage medium functions as a dielectric of an electric capacitor and the stored amount of ammonia is inferred from the capacity of this capacitor. One wall of the housing of the storage container functions as a first electrode of the capacitor, and, within the storage container, at least one additional electrode is arranged such that at least a partial amount of the storage medium forms the dielectric. The storage container may have an essentially cylindrical shape. Several cylindrical electrodes can be arranged in a coaxial manner.

8 Claims, 1 Drawing Sheet

(51) Int. Cl.
  *G01N 27/02* (2006.01)
  *F01N 11/00* (2006.01)
  *F01N 3/20* (2006.01)

(56) References Cited

U.S. PATENT DOCUMENTS

| | | |
|---|---|---|
| 6,833,272 B1 | 12/2004 | Binder et al. |
| 2005/0011183 A1 | 1/2005 | Ripper et al. |
| 2007/0204600 A1* | 9/2007 | Kubinski et al. ............... 60/286 |

FOREIGN PATENT DOCUMENTS

| | | |
|---|---|---|
| DE | 199 31 007 A1 | 1/2001 |
| DE | 101 02 237 A1 | 8/2002 |
| DE | 10 2007 060 221 A1 | 6/2009 |
| DE | 10 2008 001 004 A1 | 10/2009 |
| DE | 10 2008 040 385 A1 | 1/2010 |

OTHER PUBLICATIONS

German Search Report dated Apr. 28, 2010 with partial English translation (nine (9) pages).

* cited by examiner

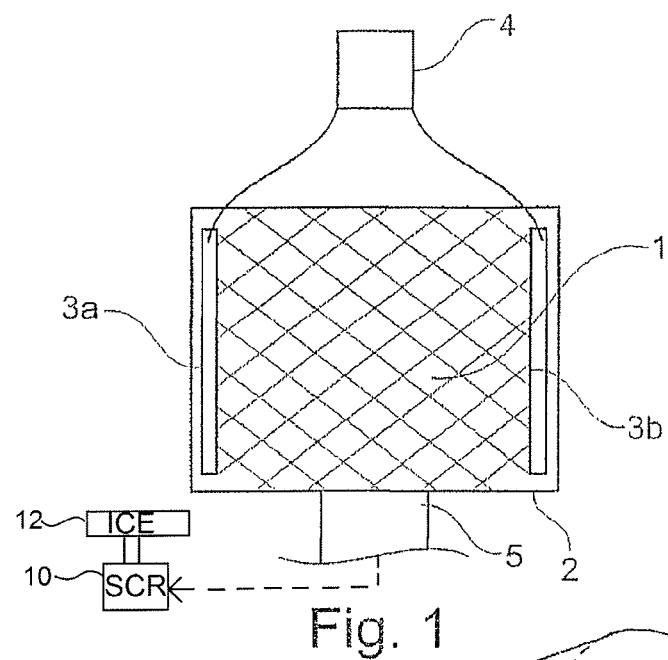
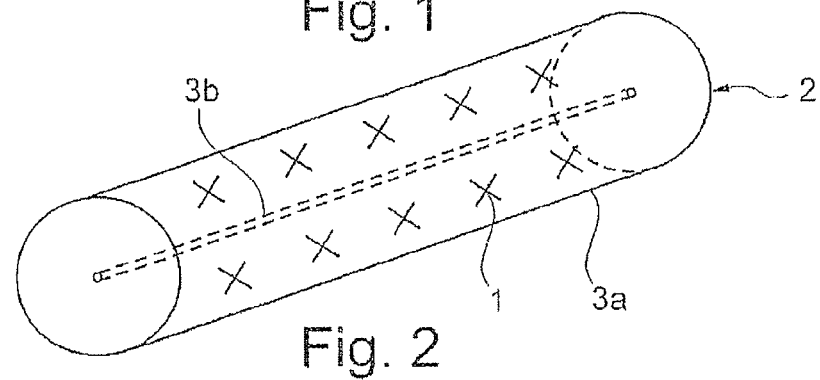
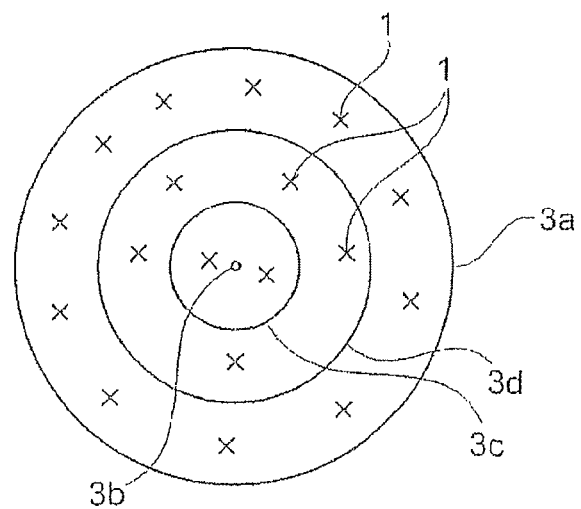
Fig. 1
Fig. 2
Fig. 3

METHOD AND STORAGE CONTAINER FOR DETERMINING A STORED AMOUNT OF AMMONIA FOR CATALYTIC EXHAUST GAS PURIFICATION

CROSS-REFERENCE TO RELATED APPLICATIONS

This application is a continuation of PCT International Application No. PCT/EP2010/055450, filed Apr. 23, 2010, which claims priority under 35 U.S.C. §119 from German Patent Application No. DE 10 2009 022 884.5, filed May 27, 2009, the entire disclosures of which are herein expressly incorporated by reference.

BACKGROUND AND SUMMARY OF THE INVENTION

The invention relates to a method for determining the amount of ammonia which is stored in a storage container by a chemical bond to a solid storage medium, in particular a salt of an earth alkaline metal or the like, and which can be released by supplying heat in order to be supplied to a catalytic exhaust gas purification device of an internal-combustion engine. The invention relates as well to a corresponding storage container. Concerning the state of the art, reference is made, for example, to German Patent document DE 197 28 343 C1.

Within the scope of so-called "SCR technology" (selective catalytic reduction technology) for the catalytic purification of internal-combustion engine exhaust gases, particularly in motor vehicles, it is known to use ammonia. The ammonia can be carried along in the vehicle in various manners, for example, as a urea solution. However, the use of so-called solid storage devices is endeavored, in which ammonia is chemically bonded in a suitable storage medium, such as strontium chloride. In this case, the ammonia is released by supplying heat to the storage medium.

Since extraction reduces the amount of ammonia stored in such a solid storage device, it is endeavored to make it possible to easily determine the residual amount of ammonia still present in the solid storage device. This can be done, for example, by weighing the solid storage device when removed from the motor vehicle.

However, for a use in motor vehicles, there is needed a measuring method that is easier and, in particular, a measuring method that can also be carried out while the vehicle is driving.

This and other needs are met according to the invention by a method for determining the amount of ammonia, which is stored in a storage container by a chemical bond to a solid storage medium, in particular a salt of an earth alkaline metal or the like, and which is releasable by supplying heat in order to be supplied to a catalytic exhaust gas purification device of an internal-combustion engine. The storage medium functions or operates as a dielectric of an electric capacitor. The stored amount of ammonia is inferred from the capacity of this capacitor.

An advantageous storage container for ammonia, by which this method can be implemented, is characterized in that the wall of the storage container functions or acts as a first electrode of an electric capacitor, and in that at least one additional electrode of this capacitor is provided within the storage container and is arranged such that at least a partial amount of the storage medium forms the dielectric of this capacitor.

It was recognized that, if the storage medium is situated directly between two appropriately shaped electrodes, a dielectric can act with respect to these electrodes when an electric voltage or voltage difference is applied to the two electrodes, so that an electric capacitor will then be present. Furthermore, it was recognized that, while the electric voltage is essentially constant and the geometrical dimensions are constant, the (electric) capacity of this capacitor will change as a function of the charging degree of the storage medium, i.e. as a function of the amount of ammonia stored in the storage medium. A simple connection can thereby be established between the basically measurable capacity of the thus formed capacitor and the charging degree of the storage medium, preferably by experimental determination; for example, in that the storage medium is weighed at different charging degrees and the respective pertaining capacity is determined. When then later a storage container with this amount of storage medium and the same electrodes is installed in the motor vehicle, as required, the capacity of the thus formed capacitor can be determined, and by way of the previously determined known connections, the degree of charging of the storage medium can be inferred.

For example, two suitably designed electrodes can be provided within a storage container, and the storage medium can be provided between these electrodes. The two electrodes, for example, can be arranged in a circular-cylindrical storage container close to the two faces of the hollow cylinder. However, for the purpose of an advantageous combination of functions, it is particularly advantageous for the housing of the storage container, which receives the storage medium, itself to form one of the two electrodes while the, or generally another, electrode is provided, for example, centrally within the storage medium. Also in the case of such a further development, in a preferred embodiment, the storage container may have an essentially cylindrical shape, in whose cylinder axis the second electrode is arranged, or whose cylinder axis is one of the two electrodes and whose generated surface is the other of the two electrodes.

However, more than two electrodes may also be provided, whereby several capacitors are formed, between which a respective partial amount of the storage medium is situated. It thereby becomes possible to individually determine the charging of this or each partial amount. For example, in a cylindrical storage container, whose wall surrounding the storage medium acts as a first electrode of a first capacitor, several cylindrical electrodes can be arranged coaxially to one another in the interior of the storage container and thus quasi in the storage medium, resulting in a quasi series connection of several capacitors. In this case, it can be provided that the capacity of each individual capacitor can be determined individually, from which a possibly different charging of the storage medium can be determined in different areas of the storage container interior.

Other objects, advantages and novel features of the present invention will become apparent from the following detailed description of one or more preferred embodiments when considered in conjunction with the accompanying drawings.

BRIEF DESCRIPTION OF THE DRAWINGS

FIG. 1 is a sectional view of a rectangular-solid-shaped storage container according to a first embodiment of the invention;

FIG. 2 is a perspective view of a cylindrical-shaped storage container according to a second embodiment of the invention; and FIG. 3 is a sectional view of a cylindrical-shaped storage container having multiple electrodes in accordance with a third embodiment of the invention.

DETAILED DESCRIPTION OF THE DRAWINGS

FIGS. 1-3 illustrate possible embodiments of the present invention, the housing of a storage container, in which a solid storage medium 1 is situated, being marked with the reference number 2. Furthermore, in each of the three embodiments according to FIGS. 1 to 3, at least two electrodes 3a, 3b are provided, which form an electric capacitor whose dielectric is formed by at least a partial amount of the solid storage medium. By way of electric lines, the electrodes 3a, 3b, as well as the possibly additional electrode(s), are connected in a suitable manner with an electronic control and analyzer unit 4 by which, on the one hand, an electric voltage or voltage difference is applied to mutually adjacent electrodes 3a, 3b, . . . , and in which the electric capacity of the electric capacitor is determined which is formed by these electrodes 3a, 3b, . . . . As described above, the amount of ammonia contained in the solid storage medium 1 situated between the above-mentioned electrodes 3a, 3b, etc. can then be inferred from the actual value for the electric capacity, for example, also in the electronic control and analyzer unit 4, in which corresponding reference values are stored.

In the embodiment according to FIG. 1, the storage container is formed by a rectangular-solid-shaped housing 2, which is shown in a sectional view in the figure, and the two electrodes 3a, 3b, between which the storage medium 1 contained in the housing 2 is situated, are fastened in a manner appropriately insulated with respect to the housing 2, to two mutually opposite walls of the housing 2. The surface of each electrode 3a, 3b is essentially equal to the surface of the pertaining housing wall. However, the latter is not an absolutely necessary characteristic. Between these two electrodes 3a, 3b, the solid storage medium 1 is situated in which ammonia is chemically bonded or can be chemically bonded. By way of an only abstractly illustrated extraction duct 5 which, penetrating the housing wall on one side of the housing 2, is connected with the interior of the housing 2 and thereby is quasi-connected with the storage medium 1, a targeted extraction of ammonia from the storage medium 1 becomes possible in a basically known manner. By means of the electric capacitor formed by the two electrodes 3a, 3b, the amount of ammonia contained in the storage medium 1 can be determined in the above-described manner. As illustrated by the dashed line, extracted ammonia is supplied to a catalytic gas purification device 10 of an internal combustion engine 12.

In the spatially illustrated embodiment according to FIG. 2, the housing 2 of the storage container has the shape of a hollow cylinder with (naturally) closed faces. In essence, in the area of the cylinder axis of this hollow cylinder, an electrode 3b is provided extending essentially along the entire length of the hollow cylinder, while the other electrode 3a of a capacitor formed of these two electrodes 3a, 3b is formed by the metallic housing 2 of the storage container, which is again completely filled (with the exception of the space required by the inner electrode 3b) with a solid storage medium 1. For reasons of simplicity, the extraction duct 5 is not shown here but is, of course, provided. The housing 2 simultaneously forming the (first) electrode can or should naturally be surrounded by an electrically insulating protective layer or an additional wall representing an electric insulator.

FIG. 3 is a sectional view of an embodiment, in which case, analogous to the embodiment according to FIG. 2, the housing 2 may have the shape of a hollow cylinder. Here, concentrically to its cylinder axis, in which (analogous to FIG. 2) the second electrode 3b is situated, several electrodes 3c, 3d, (again having the shape of hollow cylinders with a different cylinder radius) are provided in the solid storage medium 1, which (analogous to FIG. 2) is surrounded by the housing forming the so-called electrode 3a. A series connection of three electric capacitors therefore exists here, which is formed by the electrodes 3b and 3c, then by the electrodes 3c and 3d, as well as then by the electrodes 3d and 3a.

By means of the above-described method and a corresponding storage container, respectively, the charging degree of a solid storage device with ammonia or the "filling level" of ammonia can be automatically determined in a simple manner in a motor vehicle, and by way of an electronic analyzer unit, in which the above-mentioned relationship between the capacity of the capacitor and the charging degree of the storage medium is stored, can be indicated to the driver of the vehicle. This method advantageously operates completely without wear, does not result in any significant weight increase, can be implemented in a cost-effective manner and naturally supplies results that can be reproduced sufficiently accurately.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for determining an amount of ammonia in a storage container, the ammonia being stored as a chemical bond to a solid storage medium and being releasable by supplying heat, the method comprising the acts of:
    applying an electric voltage to a capacitor having at least first and second electrodes;
    measuring an electric capacity of the capacitor, in which capacitor the solid storage medium is a dielectric;
    determining the amount of ammonia stored in the solid storage medium as a function of the measured capacity; and
    wherein the ammonia is chemically bonded to a salt of an earth alkaline metal.

2. The method according to claim 1, further comprising the act of:
    releasing ammonia stored in the storage container by supplying heat; and
    supplying the released ammonia to a catalytic gas purification device of an internal-combustion engine.

3. A storage container for ammonia, the ammonia being storable by a chemical bond to a solid storage medium and releasable by supplying heat such that the released ammonia is supplyable to a catalytic exhaust gas purification device of an internal-combustion engine, the storage container comprising:
    a housing;
    at least one wall of the housing acting as a first electrode of an electric capacitor;
    at least one additional electrode of the electric capacitor being arranged within the storage container; and
    whereby at least a partial amount of the solid storage medium forms a dielectric of the capacitor.

4. The storage container according to claim 3, wherein a plurality of electrodes are provided, said plurality of electrodes forming multiple electric capacitors having different partial amounts of the solid storage medium as the dielectric.

5. The storage container according to claim 3, further comprising:
an electronic control unit operatively coupled with the capacitor, the electronic control unit determining the capacity of the capacitor and the amount of ammonia stored in the storage container as a function of the electric capacity.

6. The storage container according to claim 3, wherein the solid storage medium is a salt of an earth alkaline metal.

7. The storage container according to claim 3, wherein the storage container has a cylindrical shape;
wherein the at least one additional electrode is arranged in the cylinder axis of the storage container.

8. The storage container according to claim 4, wherein a plurality of electrodes are provided, said plurality of electrodes forming multiple electric capacitors having different partial amounts of the solid storage medium as the dielectric.

* * * * *